United States Patent [19]

Kurtz et al.

[11] 4,453,937
[45] Jun. 12, 1984

[54] DRAINAGE DEVICE WITH FLOW METER

[75] Inventors: Leonard D. Kurtz, Woodmere; Joseph LiCause, Port Jefferson Station, both of N.Y.

[73] Assignee: BioResearch Inc., Farmingdale, N.Y.

[21] Appl. No.: 290,667

[22] Filed: Aug. 5, 1981

[51] Int. Cl.³ .............................................. A61M 1/00
[52] U.S. Cl. .................................. 604/319; 604/321; 137/205
[58] Field of Search ................. 137/205; 73/198, 199, 73/200, 861.53, 861.04; 128/276, 760, DIG. 24; 604/318, 319, 320, 321, 323, 324

[56] References Cited

U.S. PATENT DOCUMENTS 3,559,647  2/1971  Bidwell et al. .................... 73/200
4,312,351  1/1982  Kurtz et al. ....................... 128/276

Primary Examiner—C. Fred Rosenbaum
Assistant Examiner—J. L. Kruter
Attorney, Agent, or Firm—Larson and Taylor

[57] ABSTRACT

A drainage device is provided with a collection chamber, an underwater seal chamber, and a separate flow chamber. The underwater seal chamber which prevents the flow of atmospheric air from the device into the pleural cavity of the patient is formed by a recessed portion in a partition separating the underwater seal chamber from the collection chamber. A passageway from the underwater seal chamber into the collection chamber is located in the partition separating the chambers and a baffle is formed around the opening to prevent excessive loss of fluid from the underwater seal chamber into the collection chamber when the device is inadvertently tilted. The flow chamber is closed off from the collection chamber and is connected with the underwater seal chamber by means of a tubular passageway adjacent the upper wall of the drainage apparatus so as to prevent fluid from passing from the underwater seal chamber into the outlet passageway. An air flow meter is provided in the flow chamber to measure the rate of air flow through the flow chamber.

13 Claims, 3 Drawing Figures

DRAINAGE DEVICE WITH FLOW METER

BACKGROUND OF THE INVENTION

The invention relates to a drainage device and more particularly to a drainage device which is designed to drain fluids from a body cavity such as the pleural cavity and to measure the flow of air through the drainage device.

It is essential for normal breathing that the space within the pleural cavity surrounding the lungs be free of liquid and be subject to a negative pressure so as to draw the lungs outwardly to fill this pleural cavity in order to permit proper breathing. Any invasion of the pleural cavity such as by lung surgery or foreign objects which pierce the ribcage or, for example, where the patient has pleurisy, generates fluids in the pleural cavity which tend to obstruct normal breathing operations. It is necessary to provide a device which can remove these fluids from the pleural cavity and, at the same time, ensure that the desired degree of negative pressure is maintained within the pleural cavity.

One of the basic types of apparatus which have been used for this purpose is shown, for example, in U.S. Pat. Nos. 3,363,626 and 3,363,627. This apparatus is known as an underwater drainage apparatus and provides three chambers, one chamber comprising a collection chamber for collecting the fluids drained from the pleural cavity through a thoracotomy tube, a second chamber known as an underwater seal chamber which protects the pleural cavity from being subject to atmospheric pressure, and a third chamber known as a pressure manometer chamber which serves to regulate the degree of negative pressure within the pleural cavity. This type of apparatus has been highly successful in both removing fluids from the pleural cavity and in maintaining the desired degree of negativity within the pleural cavity. However, such an apparatus required prefilling the underwater seal chamber with water and also prefilling the pressure manometer chamber to the desired level to maintain the desired degree of negativity within the pleural cavity. Thus, there has been a need for a drainage device which could be attached to the patient's pleural cavity and which provided a simplified structure not requiring a vacuum pump. For example, in emergency situations in the field where a vacuum pump may not be available, it is necessary to provide a device which can be attached to a patient's pleural cavity to permit drainage of fluids to allow the lungs to expand.

The drainage system disclosed in U.S. Pat. No. 4,015,603 provided an apparatus which may or may not be used with a vacuum source. The underwater seal in this system is located at the lower end of the thoracotomy tube at the upper end of the drainage device. In the device shown in this prior patent, the underwater seal is formed by liquid drained from the patient's pleural cavity. The location of the underwater seal chamber at the lower end of the thoracotomy tube as disclosed in U.S. Pat. No. 4,015,603 created a problem in certain unusual circumstances. In a case of a patient having a blockage in the bronchial tubes, such that the patient was having severe problems in getting air into the lungs, exceedingly high negativity was being created in the pleural cavity. Such high negativity caused the fluid in the underwater seal to be drawn upwardly through the thoracotomy tube and, if the degree of negativity was sufficiently high, it was possible for fluid to reenter the pleural cavity. This condition of fluid from the underwater seal chamber reentering the pleural cavity could cause infection or otherwise create problems for the patient. In addition, it was possible to entirely lose the seal provided by the underwater seal chamber during periods of high negativity in the pleural cavity. The loss of the water seal has a potential for serious damage in the event the suction becomes disconnected or the device is used as a two bottle system with the collection chamber open to atmosphere.

In U.S. Pat. No. 3,853,128 there is disclosed a positive pressure relief valve in a drainage apparatus having a conventional underwater seal and manometer chamber. The positive pressure relief valve is disposed between the underwater seal and manometer chambers and provides relief from high pressure surges within the collection chamber. The device disclosed in U.S. Pat. No. 3,853,128 must, however, be prefilled prior to use and does not function as a two chambered device which is usable without prefilling. In U.S. Pat. No. 3,559,647 there is disclosed an underwater drainage apparatus having seal which is provided with a gas flow meter at the bottom of the seal. The gas flow meter is comprised of a series of orifices located at the bottom of the underwater seal. The more orifices which gas passes through, the greater the gas flow. However, this type of flow meter is suitable only for indicating the gas flow in steps.

SUMMARY OF THE INVENTION

In accordance with the invention an improved medical drainage device for draining fluids from the body of a patient is provided which enables the operator to monitor the air flow through the device. The air flow meter is simple and rugged in construction and efficient and dependable in use. According to the invention, the surgical drainage apparatus comprises a housing with an outlet which is connected to a suitable source of suction so that fluids can be drawn into the housing through a fluid inlet. A collection chamber is formed in the housing which receives the fluids from the patient and a partition extending across a portion of the housing forms an underwater seal chamber beneath the inlet. A tubular extension connected to the inlet projects downwardly into the underwater seal chamber to provide a fluid seal. An air flow meter means is fluidly associated with the outlet means to measure the rate of flow of air through the outlet means. The apparatus of the invention is completely "dry" prior to use, i.e., does not require any prefilling by the user.

In a preferred embodiment of the invention, the air flow meter means includes a flow chamber and a passageway extending from the underwater seal chamber to the flow chamber. An air flow meter is located in the flow chamber. Preferably, an inhibiting means inhibits the accidental flow of liquids into the air flow meter. The inhibiting means can be a vertical baffle around the opening of the partition or a trap at the end of the passageway prior to the air flow meter. The air flow meter is an enclosed elongate column having a horizontal cross-sectional dimension which increases in size upwardly and an air flotation element movably disposed in the column which is lifted by the flow of air. A one-way valve is also provided to permit the escape of gases from within the collection chamber when the pressure within the chamber is higher than atmospheric but which otherwise prevents the passage of air from the atmosphere to the collection chamber. When the drainage device is used with regulated suction, a positive pressure release valve is included to prevent the build-up of excessive positive pressure within the device in the event of failure of the suction pump or in the event of a sudden, very high pressure surge within the pleural cavity.

Additional features and advantages of the present invention will be apparent from a consideration of the following detailed description of the preferred embodiments of the invention in connection with the accompanying drawings.

DETAILED DESCRIPTION OF THE PREFERRED EMBODIMENTS

Figure 1:
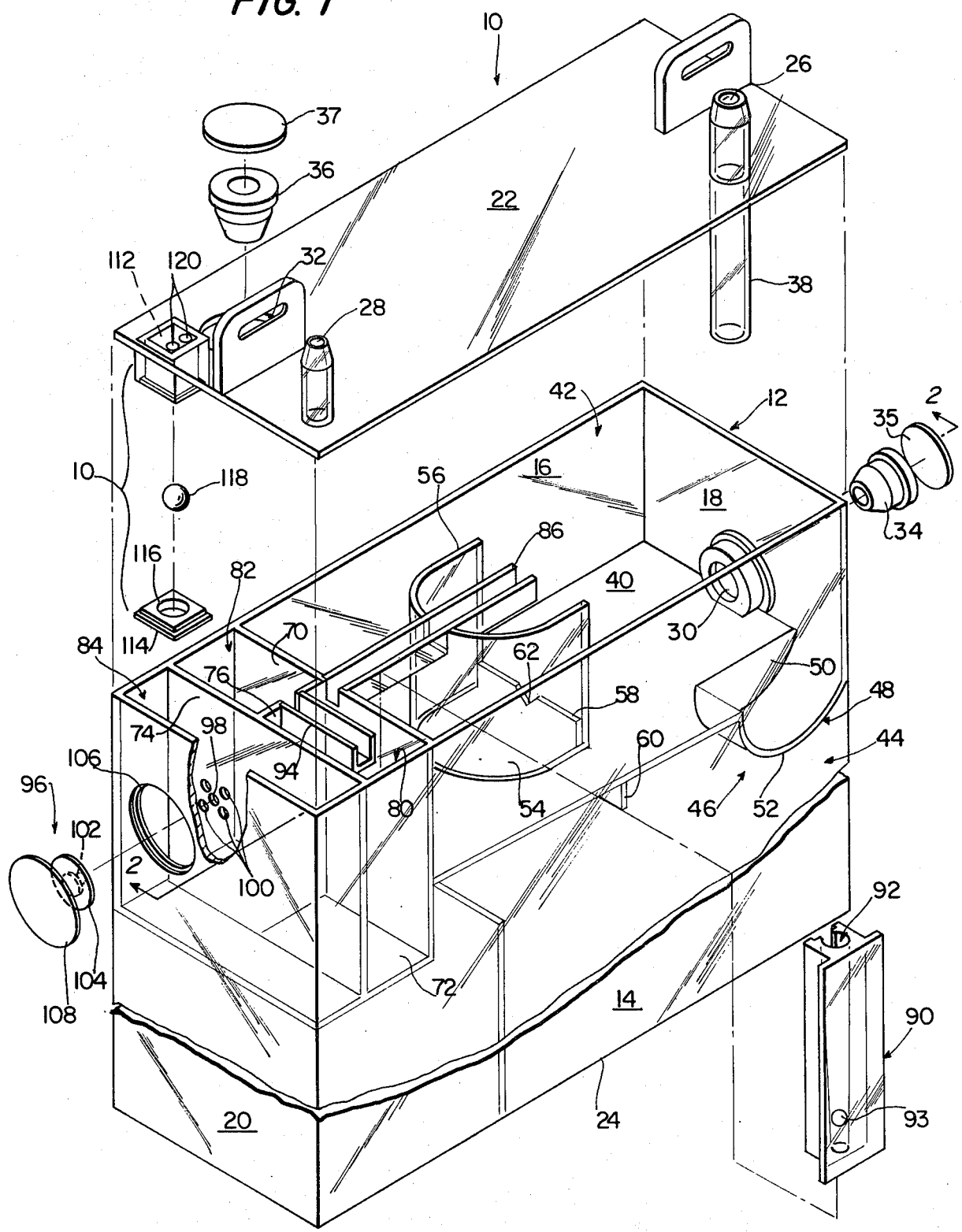
FIG. 1 is a perspective view of the two-chambered underwater drainage device with a flow meter according to the present invention.
Figure 2:
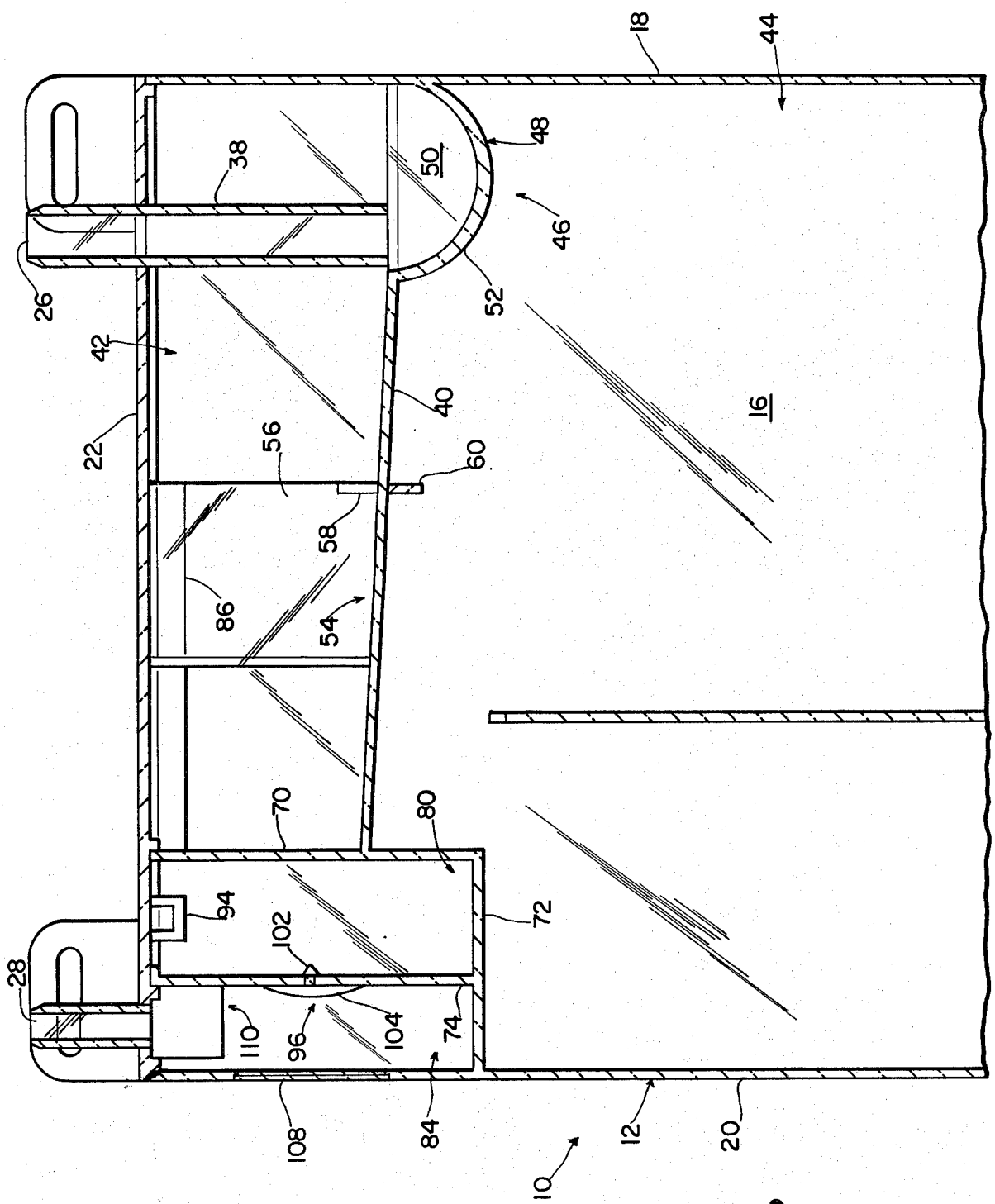
FIG. 2 is a front cross-sectional elevation view of the of the drainage device depicted in FIG. 1 taken along line 2—2.

Referring now more specifically to the drawings where like numerals are used to represent like elements throughout the several views, there is depicted in FIGS. 1 and 2 an underwater drainage device 10 that comprises a housing 12 which may be formed of a rigid transparent plastic material or the like. Housing 12 is depicted in the present embodiment in a substantially box-like shape having four vertical walls when in the upright position, namely a front wall 14, a rear wall 16, a first end wall 18, and a second end wall 20. In addition, housing 12 is provided with a top wall 22 and a bottom wall 24.

Underwater drainage device 10 is also provided with an inlet 26 for attachment to a thoracotomy tube which extends into the patient's pleural cavity. An outlet 28 is adapted to connect housing 12 with a suitable source of suction. Housing 12 is further provided with a first opening 30 in the upper portion of first end wall 18 and a second opening 32 located adjacent outlet 28. Grommets 34 and 36, respectively, are disposed in first opening 30 and second opening 32. Removable covers 35 and 37 are positioned in sealing engagement with container 12 over respective grommets 34 and 36.

As shown in FIGS. 1 and 2, an internal inlet tube 38 extends downwardly from drainage device inlet 26 and terminates at a sloping main partition 40. Main partition 40 extends horizontally from first end wall 18 toward second wall 20 and transversely from front wall 14 to rear wall 16 to divide drainage device 10 into an upper underwater seal chamber 42 and a lower collection chamber 44. One corner of main partition 40, located below inlet tube 38, is provided with a U-shaped recessed portion 46. Recessed portion 46 is defined by a cup portion 48 having a semicircular side 50 attached to a circular bottom 52. The other side of cup portion 48 is formed by front wall 14.

Cup portion 48 is located and sized so as to satisfy two, somewhat conficting criteria. The purpose of cup portion 48 is to retain liquid drained form the pleural cavity so that after a predetermined amount of liquid has been drained and the bottom of inlet tube 38 is covered, a seal is automatically formed. Thus, one criterion is that cup portion 48 be small enough so that only a relatively little amount of liquid need by drained from the pleural cavity of the patient before a seal is formed. On the other hand, it is an important feature of the present invention that the seal, once formed, is not destroyed by the inadvertent tilting of drainage device 10. Hence, cup portion 48 should have a sufficiently large enough capacity so that should some liquid be lost therefrom, the seal will not be broken. Obviously, the bottom of inlet tube 38 can extend downwardly into cup portion 48 to aid in preventing the loss of a seal if drainage device 10 becomes tilted. However, this has a disadvantage in that the greater the height of the liquid up inlet tube 38, the greater the differential in pressure will be between the pleural cavity and the seal chamber. Therefore, in a presently preferred embodiment of the present invention, the bottom of inlet tube 38 extends only to the bottom of main partion 40. As mentioned above, main partition 40 is sloped from a position nearer second end wall 20 to first end wall 18. Thus, main partition 40 is spaced at a greater distance from top wall 22 adjacent end wall 18 than at the position nearer second end wall 20. The sloping of main partition 40 permits the liquid accumulating in seal chamber 42 to flow in the direction of cup portion 48, thereby tending to keep cup portion 48 filled upon a minor tilting of drainage device 10.

Located substantially centrally in main partition 40 is an opening 54 for permitting the flow of fluid (i.e., both liquid and gas) from underwater seal chamber 42 into collection chamber 44. As shown, means surrounding opening 54 is provided to prevent a substantial loss of liquid from underwater seal chamber 42 into collection chamber 44 should drainage device 10 be tipped. This means includes a U-shaped baffle 56 that extends between main partition 40 and top wall 22. The open end of baffle 56 faces first end 18 and is aligned substantially parallel therewith. A gate 58 is connected at each end to the open ends of baffle 56, and is also connected at the bottom to main partition 40. Gate 58 extends upwardly a predetermined distance toward top wall 22 such that the depth of liquid in underwater seal chamber 42, when drainage device 10 is in the normal upright position, is determined by the height of gate 58. Thus, as soon as the liquid drained from the pleural cavity accumulates in underwater seal chamber 42 to a depth greater than the height of gate 58, the extra liquid flows over gate 58 through opening 54 into collection chamber 44 below. A drip ledge 60 is located on the underside of main partition 40 directly below the bottom of gate 58. Drip ledge 60 permits a more efficient flow of the overflow liquid from underwater seal chamber 42 into collection chamber 44. As shown in FIG. 1, a notch 62 can be centrally provided in gate 58 so as to more accurately control the depth of the reservoir liquid in underwater seal chamber 42.

A vertical partition 70 is attached to the end of partition 40 near second end wall 20. Vertical partition 70 extends transversly between front wall 14 and rear wall 16 and vertically extends between top wall 22 and a floor 72. Floor 72 extends horizontally from vertical partition 70 to second end wall 20 and from front wall 14 to rear wall 16. Vertical partition 70 and floor 72 form a corner chamber in housing 12 which is further subdivided by a second vertical partition 74 parallel to vertical partition 70 and a transverse partition 76 located between vertical partition 70 and second vertical partition 74. As shown best in FIG. 1, this forms three separate chambers in the corner of housing 12: a flow chamber 80, a connecting chamber 82, and an outlet chamber 84.

Fluid communication is provided between upper seal chamber 42 and flow chamber 80 by a channel passageway 86. As shown best in FIG. 1, passageway 86 extends along top wall 22 from one end which is located above gate 58, through baffles 56, to the other end which terminates at vertical partition 70.

Disposed along front wall 14 in flow chamber 80 is a flow meter 90. Flow meter 90 includes an enclosed elongate column 92 extending in a generally vertical direction. The horizontal cross-sectional dimension of column 92 increases gradually in size upwardly over the length thereof. It should be noted that the lower end of column 92 is spaced slightly above floor 72. The upper end of column 92 is fluidly connected to a second channel passageway 94. As shown in FIG. 1, second channel passageway 94 extends from column 92 along top wall 22 to transverse partition 76.

Connecting chamber 82 lies below grommet 36 which is positioned in top wall 22. Thus, access to connecting chamber 82 can be provided through grommet 36 when desired. One-way fluid communication out of connecting chamber 82 and into outlet chamber 84 is provided through a suitable one-way valve 96 located on second vertical partition 74. Disclosed in one of the applicants' prior U.S. Applications, Ser. No. 107,329, filed Dec. 26, 1979 and entitled DRAINAGE DEVICE WITH SEPARATE OUTFLOW CHAMBER now U.S. Pat. No. 4,312,351 issued Jan. 26, 1982 and Serial No. 120,295, filed Jan. 11, 1980 and entitled TWO-CHAMBER UNDERWATER DRAINAGE APPARATUS WITH ONE-WAY OUTFLOW VALVE now U.S. Pat. No. 4,324,244 issued Apr. 13, 1982, incorporated herein by reference, is a suitable construction for a one-way valve 96. As shown by these prior applications and in FIGS. 1 and 2, a central orifice 98 and four peripheral orifices 100 extend through second partition 74. One-way valve 96 has a stem 102 that is mounted in central orifice 98 and an enlarged head 104 that extends over peripheral orifices 100. Thus, when pressure in underwater seal chamber 42, collection chamber 44, flow chamber 80, and connecting chamber 82 exceeds the pressure in outlet chamber 84, head 104 of one-way valve 96 is forced away from second vertical partition 74 so as to permit the passage of gases into outlet chamber 84 and to equalize the pressures therebetween. However, when the pressure is higher within outlet chamber 84 than within the rest of drainage device 10, one-way valve 96 remains closed preventing fluid communication in the opposite direction. For convenience, a suitable aperture 106 located in second end wall 20 is provided for inserting head 104 into position on second vertical partition 74. Aperture 106 is then sealed by a cover 108.

Outlet chamber 84 is fluidly connected to a suitable source of suction or to the atmosphere through outlet 28 in top wall 22 which is positioned above outlet chamber 84. Extending downwardly from top wall 22 and into outlet chamber 84 is a positive pressure release valve 110. The purposes for and the detailed structure of release valve 110 are described in greater detail in the aforementioned pending patent applications of one of the inventors. Release valve 110 includes an enclosed valve chamber 112 having a bottom 114 with an aperture 116 therein. A ball 118 is located in valve chamber 112 and is normally seated on aperture 116. Fluid communication is provided between valve chamber 112 and the outside atmosphere through two valve outlets 120 in top wall 22 located above valve chamber 112. The purpose of positive pressure release valve 110 is to provide a means for release of high positive pressure to atmosphere in the event very high pressures are reached within collection chamber 44, underwater seal chamber 42, flow chamber 80, connecting chamber 82, and outlet chamber 84 and the device is operated with a vacuum pump which is malfunctioning or unable to provide release for such high pressure. Normally, ball 118 remains seated over aperture 116 to maintain release valve 110 closed and release valve 110 opens only in response to pressures within drainage device 10 in excess of atmospheric pressure.

When drainage device 10 is used, it is normally used with a suction attached to outlet 28 from a controlled suction device. However, in some cases, drainage device 10 can also be used without a suction. In either case, drainage device 10 is used without prefilling the fluid seal. A thoracotomy tube (not shown) is connected between the pleural cavity of the patient and inlet 26. One-way outlet valve 96 protects the patient from the admission of atmospheric air with the resulting danger of pneumothorax. The liquid secretions from the pleural cavity initially fill cup portion 48 to provide an underwater seal at the lower end of inlet tube 38. When cup portion 48 is filled with liquid, the liquid overflows onto the top of main partition 40, Initially, accurate measurements of the liquid secretion can be made inside cup portion 48, which can be calibrated.

In the event that suction is used, the hose from a regulated suction source is attached to outlet 28 and the desired degree of negativity is maintained within collection chamber 44, underwater seal chamber 42, and the pleural cavity. When operated with suction, additional protection is provided against possible buildup of positive pressure within collection chamber 44 and the pleural cavity of the patient by positive pressure release valve 90, which can open in the event of sudden high pressure surges within drainage device 10.

In the use of drainage device 10 wherein the underwater seal is formed directly at the end of internal inlet tube 38 by the liquid secretions from the pleural cavity of the patient, it is important that drainage device 10 be constructed so that excessive negativity within the pleural cavity, such as might by caused by blockage in the bronchial tubes or the like, cannot cause the fluid within the underwater seal to rise within inlet tube 38 and into the throacotomy tube and pass back into the pleural cavity. This is precluded in the presently disclosed apparatus because of the incorporation of one-way valve 96.

As drainage device 10 operates to collect fluids from the pleural cavity, gases which are passed from the pleural cavity into device 10 through inlet 26 are subsequently conducted out of drainage device 10. These gases pass through channel passageway 86, into flow chamber 80, into flow meter 90 and the bottom of column 92, out of the top of column 92 into second channel passageway 94, into connecting chamber 82, through one-way valve 96, into outlet chamber 84, and finally out of drainage device 10 through outlet 28. The rate of flow of these gases is indicated by ball 118 which rises in column 92. As discussed above, column 92 increases in cross-sectional dimension upwardly so that ball 118 rises to a height in column 92 which is indicative of the specific rate of flow of gases through column 92. The rise of ball 93 is visible through front wall 14 so that the rate of flow of gases through drainage device 10 is easily discernable. The rate of flow of gases is important in determining whether drainage device 10 is functioning properly and whether an air leak exists in the pleural cavity of the patient. Where an air leak does exist in the pleural cavity of the patient, the greater the flow of air through flow meter 90, the greater the air leak present in the patient's pleural cavity.

If drainage device 10 is accidentally tipped or tilted, because of U-shaped baffle 56 and the location of channel passageway 86, an inhibiting means is provided to prevent the flow of fluids from underwater seal chamber 42 into flow chamber 80. The introduction of liquids into flow chamber 80 would cause flow meter 90 to malfunction. It sould be noted that during an accidental tilting, gate 58 blocks the entrance of fluid through opening 54 in main partition 40 and together with the sloping of main partition 40 assure that a sufficient reservoir of liquid is maintained in seal chamber 42 to keep cup portion 48 full of liquid and the seal intact.

Figure 3:
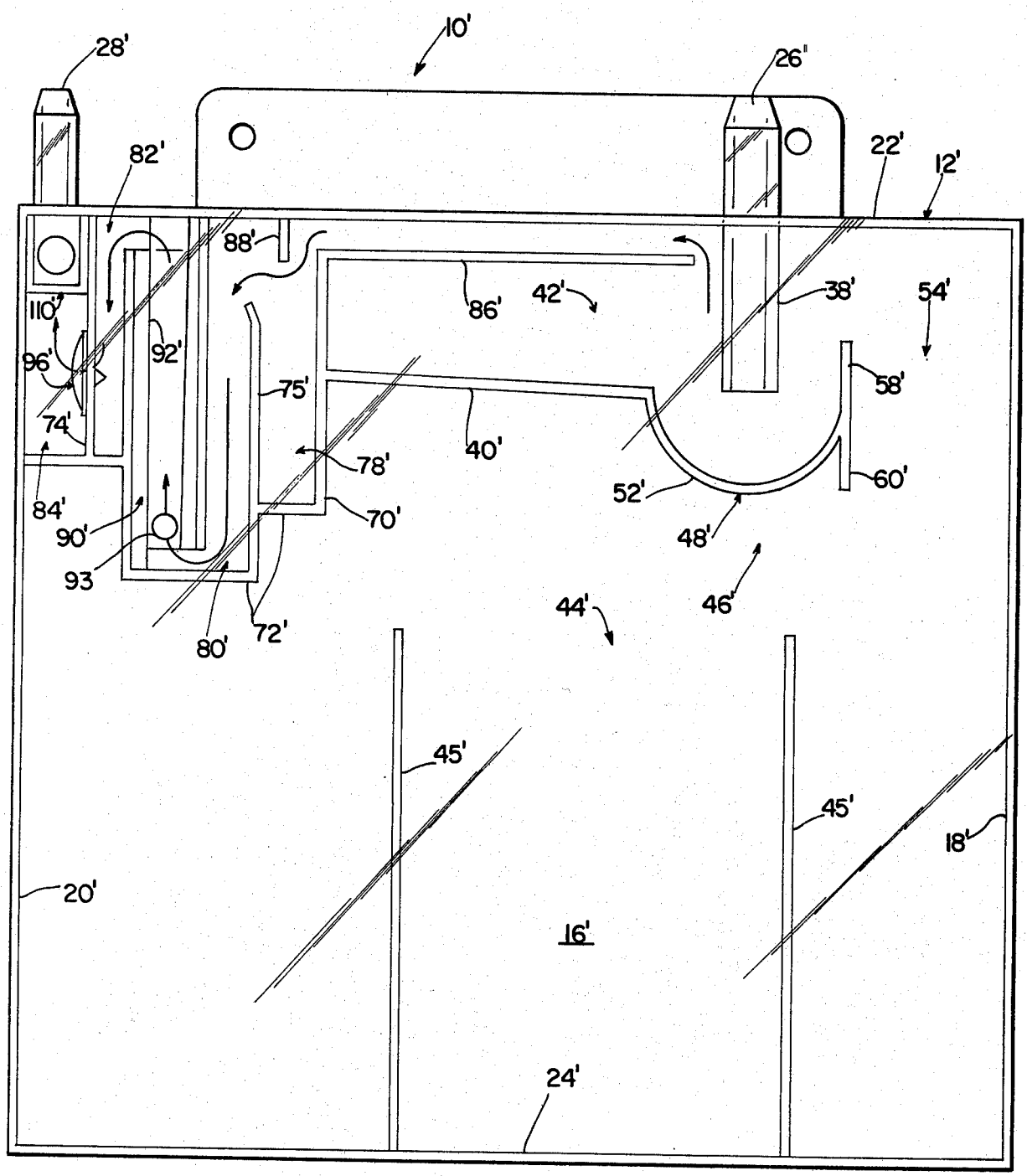
FIG. 3 is a front cross-sectional elevation view of an alternative embodiment of a drainage device with a flow meter.

Depicted in FIG. 3 is an alternative embodiment of the present invention which includes a drainage device 10' which is similar in many respects to drainage device 10. Thus, drainage device 10' has a housing composed of a front wall, a rear wall 16', a first end wall 18', a second end wall 20', a top wall 22', and a bottom wall. Top wall 22' includes an inlet 26' and an outlet 28'. Depending from inlet 26' is internal inlet tube 38'. Housing 12' is divided horizontally by a main partition 40' to form an underwater seal chamber 42' and a lower collection chamber 44'. Lower collection chamber 44' is further divided into three collection wells by vertical walls 45'.

Main partition 40' includes a recessed portion 46' having a cup portion 48'. Main partition 40' is spaced from first end wall 18' so as to provide an opening 54' between underwater seal chamber 42' and lower collection chamber 44'. Located adjacent opening 54' is a gate 58' extending above main partition 40' and a drip ledge 60' located immediately below gate 58'.

In this embodiment, a vertical partition 70' and a floor 72' separate a corner of housing 12' from underwater seal chamber 42' and lower collection chamber 44'. A second vertical partition 74' and a trap partition 75' further divide the corner of housing 12' into a trap chamber 78', a flow chamber 80', a connecting chamber 82', and an outlet chamber 84'. A channel passageway 86' running along the underside of top wall 22' connects underwater seal chamber 42' with trap chamber 78'. Adjacent the end of channel passageway 86' and in the center of trap chamber 78' is a drip ledge 88'. An air flow meter 90' having a column 92' is disposed vertically in flow chamber 80'. The bottom of column 92' is located adjacent, but spaced from, floor 72' while the top of column 92' is open to connecting chamber 82'. Housing 12' is further provided with a one-way valve 82' and a positive pressure release valve 110' similar to one-way valve 96 and release valve 110 described above.

In use, drainage device 10' functions in the same manner as described above with respect to drainage device 10. Thus, inlet 26' is connected by a thoracotomy tube to the pleural cavity of the patient and outlet 28' is preferably connected to a suitable source of suction. As fluids from the patient collect in cup portion 48', an underwater seal is quickly formed with internal inlet tube 38'. As sufficient liquid collects, additional liquid overflows gate 58' and is collected in the first well in collection chamber 44'. In the mean time, gases which are conducted through the thoracotomy tube pass through internal inlet tube 38', into underwater seal chamber 42', into channel passageway 86', through trap chamber 78', into flow chamber 80', through flow meter 90', into connecting chamber 82', through one-way valve 96', into outlet chamber 84', and finally out of housing 12' through outlet 28'. The rate of flow of the gases is determined by flow meter 90' on the same manner as discribed above with respect to flow meter 90.

Should housing 12 be inadvertently tilted towards first and wall 18, gate 58' acts to maintain the fluid in underwater seal chamber 42. Should housing 12 be tilted inadvertently in the other direction, the fluid pools in the area between vertical partition 75' and main partition 40'. Thus, with channel passageway 86' located along top wall 22', the fluid in underwater seal chamber 42' is inhibited from entering channel passageway 86' while still being retained in underwater seal chamber 42'.

If liquid from underwater seal chamber 42' should inadvertently enter channel passageway 86', the liquid continues along channel passageway 86' until it drips into trap chamber 78'. To assure that the liquid falls into trap chamber 78', drip ledge 88' is positioned so as to prevent any of the liquid from being drawn directly from channel passageway 86' into flow chamber 80'. Obviously, any liquid collecting or impinging on drip ledge 88' falls into trap chamber 78'. The top angled portion of trap partition 75' also helps to maintain any liquid in the gas flow exiting from channel passageway 86' from passing into flow chamber 80'. As the front wall of housing 12' is preferably made from a transparent plastics material, the presence of liquids in trap chamber 78' is immediately viewable. Thus, if any liquids are seen in trap chamber 78', the use of drainage device 10' should be immediately discontinued and replaced with a new drainage device 10' because of the danger of the liquid blocking air flow meter 90' which could result in a tendin pneumothorax.

While drainage devices 10 and 10' can rest on their bottom walls, it would also be possible to provide drainage devices 10 and 10' with a hanger attachment to further stabilize the device or to allow the device to be hooked on to a bedside. Such a hanger device is also disclosed in the above mentioned pending applications.

Although the invention has been described relative to exemplary embodiments thereof, it will be understood that variations and modifications can be effected in these exemplary embodiments without departing from the scope and spirit of the invention.

We claim:

1. A drainage device comprising a closed container, an inlet to said container for connection with a thoracotomy tube, a partition extending across at least a portion of the upper end of said container, a recess formed in said partition beneath said inlet, a tubular inlet member extending downwardly from said inlet to said recess so that liquid in the recess forms a underwater seal with the lower end of the inlet member, an outlet from said closed container, an outlet chamber formed within said container enclosing said outlet, a oneway valve disposed in an inlet opening in a wall of said outlet chamber permitting fluid flow from said container inlet to said outlet and preventing fluid flow in the opposite direction, and a passageway connecting said inlet opening of said outlet chamber with the remaining volume of said container, said passageway including a series of contiguous vertically extending interconnecting conduits interconnectd such that fluid flowing from the container inlet to the outlet follows a tortuous path, including two bends of substantially 180 degrees within said series of vertically extending conduits.

2. A drainage device according to claim 1 and further including a positive pressure relief valve disposed in said container connecting said container with atmosphere to relieve positive pressure within said container.

3. A drainage device according to claim 2 wherein said positive pressure relief valve is disposed in a wall of said outlet chamber on the outlet side of said oneway valve to form a passageway to atmosphere in parallel with said outlet from said outlet chamber.

4. A drainage device according to claim 1 and further including air flow meter means disposed in said passageway.

5. A drainage device according to claim 5 wherein said air flow meter means includes a flow chamber said in said housing which is fluidly connected to said outlet means and an air flow meter located in said flow chamber, said air flow meter being fluidly disposed between said passageway and said outlet means so that the rate of gas flow is measured by said air flow meter.

6. A drainage device according to claim 5 and further including an inhibiting means for inhibiting the accidental flow of liquid into said air flow meter.

7. A drainage device according to claim 6 wherein said inhibiting means includes a substantially vertical baffle extending around the periphery of said opening in said partition.

8. A drainage device as claimed in claim 7 wherein said passageway extends through said baffle and opens into the underwater seal chamber above said opening in said partition.

9. A drainage device as claimed in claim 8 wherein said passageway extends along the upper portion of said housing.

10. A drainage device as claimed in claim 6 wherein said inhibiting means includes a trap means disposed fluidly between said passageway and said flow chamber for collecting liquids passing through said passageway.

11. A drainage device as claimed in claim 10 wherein said trap chamber is visible from outside of said container so that the presence of any liquid in said trap chamber is readily discernible.

12. A drainage device comprising:
a housing;
a collection chamber formed in said housing for receiving liquids and gases from the body of a patient;
an inlet at the upper end of said housing;
a partition extending across a portion of the housing to form an underwater seal chamber beneath said inlet;
a tubular extension connected to said inlet and projecting downwardly into said underwater seal chamber whereby liquids from the body of a patient are collected in the underwater seal chamber and provide a liquid seal with the lower end of said tubular extension;
outlet means for providing an outlet to the atmosphere from said housing;
an air flow meter means fluidly associated with said outlet means for measuring the rate of flow of gases through said outlet means;
said air flow meter means including a flow chamber located in said housing which is fluidly connected to said outlet means; a passageway fluidly connecting the underwater seal chamber with said flow chamber through which gases flow; and an air flow meter located in said flow chamber, said air flow meter being fluidly disposed between said passageway and said outlet means so that the rate of gas flow is measured by said air flow meter and said air flow meter including an enclosed elongate column disposed in a generally vertical orientation having a horizontal cross-sectional dimension which increases in size upwardly over the length of said column; an air inlet located in said column adjacent the lower end thereof; an outlet located in said column adjacent the upper end thereof; and an air flotation element movably disposed in said column so as to be lifted in said column by the flow of gases from said passage to said outlet means, said air flotation element being sized so as to fit relatively closely within said column such that, due to the increase in cross-sectional dimension of said column, the position of said air flotation element is indicative of the rate of flow of gases through said flow chamber.

13. A drainage device comprising:
a housing;
a collection chamber formed in said housing for receiving liquids and gases from the body of a patient;
an inlet at the upper end of said housing;
a partition extending across a portion of the housing to form an underwater seal chamber beneath said inlet;
a tubular extension connected to said inlet and projecting downwardly into said underwater seal chamber whereby liquids from the body of patient are collected in the underwater seal chamber and provide a liquid seal with the lower end of said tubular extension;
outlet means for providing an outlet to the atmosphere from said housing;
an air flow meter means fluidly associated with said outlet means for measuring the rate of flow of gases through said outlet means;
said air flow meter means including a flow chamber located in said housing which is fluidly connected to said outlet means; a passageway fluidly connecting the underwater seal chamber with said flow chamber through which gases flow; and an air flow meter located in said flow chamber, said air flow meter being fluidly disposed between said passageway and said outlet means so that the rate of gas flow is measured by said air flow meter;
said air flow meter including an enclosed elongate column disposed in a generally vertical orientation having a a horizontal cross-section dimension which increases in size upwardly over the length of said column; an air inlet located in said column adjacent the lower end thereof; an outlet located in said column adjacent the upper end thereof; and an air flotation element movably disposed in said column so as to be lifted in said column by the flow of gases from said passage to said outlet means, said air flotation element being sized so as to fit relatively closely within said column such that, due to the increase in cross-sectional dimension of said column, the position of said air flotation element is indicative of the rate of flow of gases through said flow chamber; and
said outlet means further including a positive pressure relief valve located between said one-way valve and the atmosphere.

* * * * *